US006896234B2

United States Patent
Henley et al.

(10) Patent No.: US 6,896,234 B2
(45) Date of Patent: May 24, 2005

(54) RAIL SYSTEM FOR SUPPORTING AND MOVING A PATIENT GANTRY

(75) Inventors: Alan W. Henley, Knoxville, TN (US); Charles A. Brenner, Friendsville, TN (US); Mark S. Hawley, Knoxville, TN (US)

(73) Assignee: CTI PET Systems, Inc., Knoxville, TN (US)

( * ) Notice: Subject to any disclaimer, the term of this patent is extended or adjusted under 35 U.S.C. 154(b) by 51 days.

(21) Appl. No.: 10/413,836

(22) Filed: Apr. 15, 2003

(65) Prior Publication Data

US 2004/0206880 A1 Oct. 21, 2004

(51) Int. Cl.[7] .................................................. F16M 1/00
(52) U.S. Cl. ........................ 248/647; 238/10 R; 384/45
(58) Field of Search ............................... 248/647, 650, 248/656, 658, 675, 188.4; 378/195–198; 384/21, 59, 45, 55; 403/330; 238/10 R; 104/249, 250, 252, 238, 151, 166

(56) References Cited

U.S. PATENT DOCUMENTS

| 192,314 | A | * | 6/1877 | Wheaton ..................... 104/213 |
| 685,851 | A | * | 11/1901 | Kifer et al. .................. 285/311 |
| 988,029 | A | * | 3/1911 | Prellwitz .................... 279/19.1 |
| 2,524,959 | A | * | 10/1950 | Clark ........................ 238/10 R |
| 3,216,678 | A | * | 11/1965 | Foedisch .................... 248/694 |
| 4,644,869 | A | * | 2/1987 | Rhodes ..................... 104/172.2 |
| 4,876,785 | A | * | 10/1989 | Driggers ..................... 29/426.3 |
| 5,251,732 | A | * | 10/1993 | Bruning ................. 191/22 DM |
| 5,380,099 | A | * | 1/1995 | Teramachi .................... 384/45 |
| 5,460,452 | A | * | 10/1995 | Hara ........................... 384/45 |
| 5,495,809 | A | * | 3/1996 | Carbo ...................... 105/157.1 |
| 5,549,050 | A | * | 8/1996 | Rhodes .................... 104/172.3 |
| 5,678,663 | A | * | 10/1997 | Watanabe et al. ............. 188/67 |
| 5,944,383 | A | * | 8/1999 | Mathey et al. .............. 297/341 |
| 6,203,196 | B1 | * | 3/2001 | Meyer et al. ............... 378/197 |
| 6,490,476 | B1 | | 12/2002 | Townsend et al. |
| 6,557,775 | B1 | * | 5/2003 | Brinson et al. .......... 238/10 R |
| 6,663,286 | B2 | * | 12/2003 | Shimizu et al. ............... 384/45 |
| 2002/0014573 | A1 | * | 2/2002 | Anderson ................... 248/677 |
| 2003/0039413 | A1 | * | 2/2003 | Tsukada et al. ............... 384/45 |

* cited by examiner

*Primary Examiner*—Korie Chan
(74) *Attorney, Agent, or Firm*—Pitts & Brittian, PC

(57) ABSTRACT

A rail system for supporting a patient gantry including a fixed rail assembly mounted on a support surface and a service rail assembly releasably securable to the fixed rail assembly. Each rail assembly includes a bar and a top rail. An alignment device is provided for aligning the top rails of each assembly and is configured so that the rails cannot be interchanged. A lever is provided for positively securing the service rail assembly to either the fixed rail assembly or in a first receptor defined by a mounting block secured to a bearing block and on which is mounted the patient gantry. A toggle clamp includes a pin selectively received in a locating hole defined in the fixed rail assembly. If the toggle clamp has not been engaged and the lever does not engage the first receptor, the lever is received by a second receptor to prevent derailment.

24 Claims, 8 Drawing Sheets

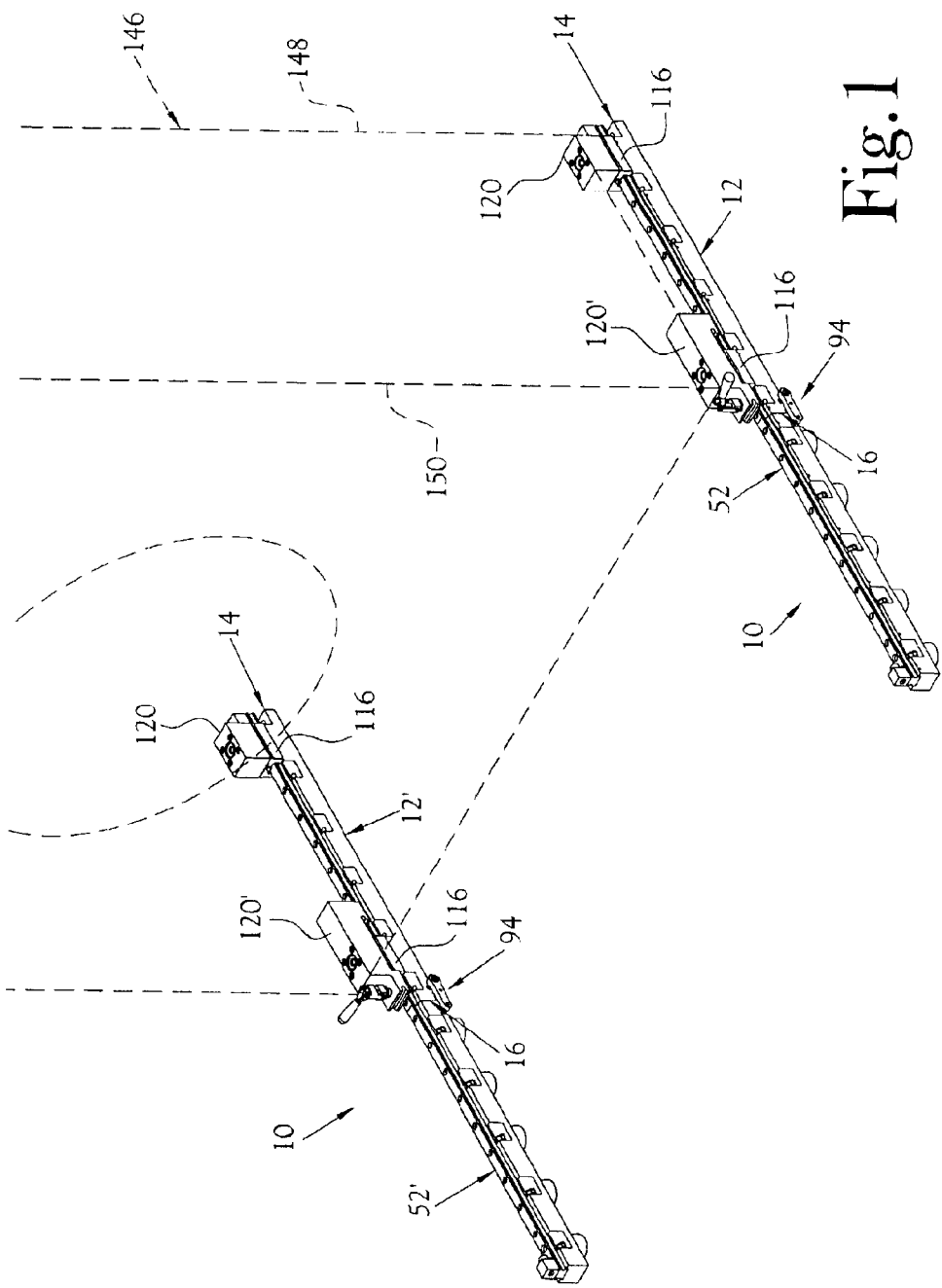

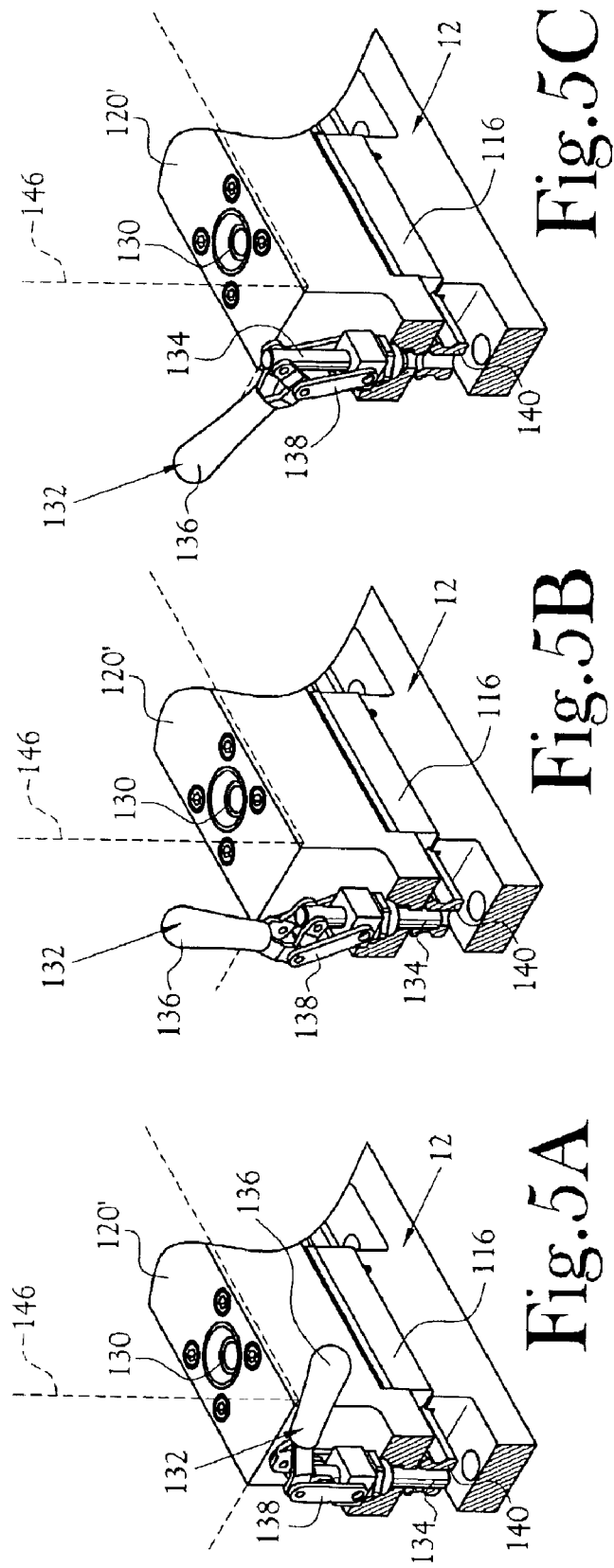

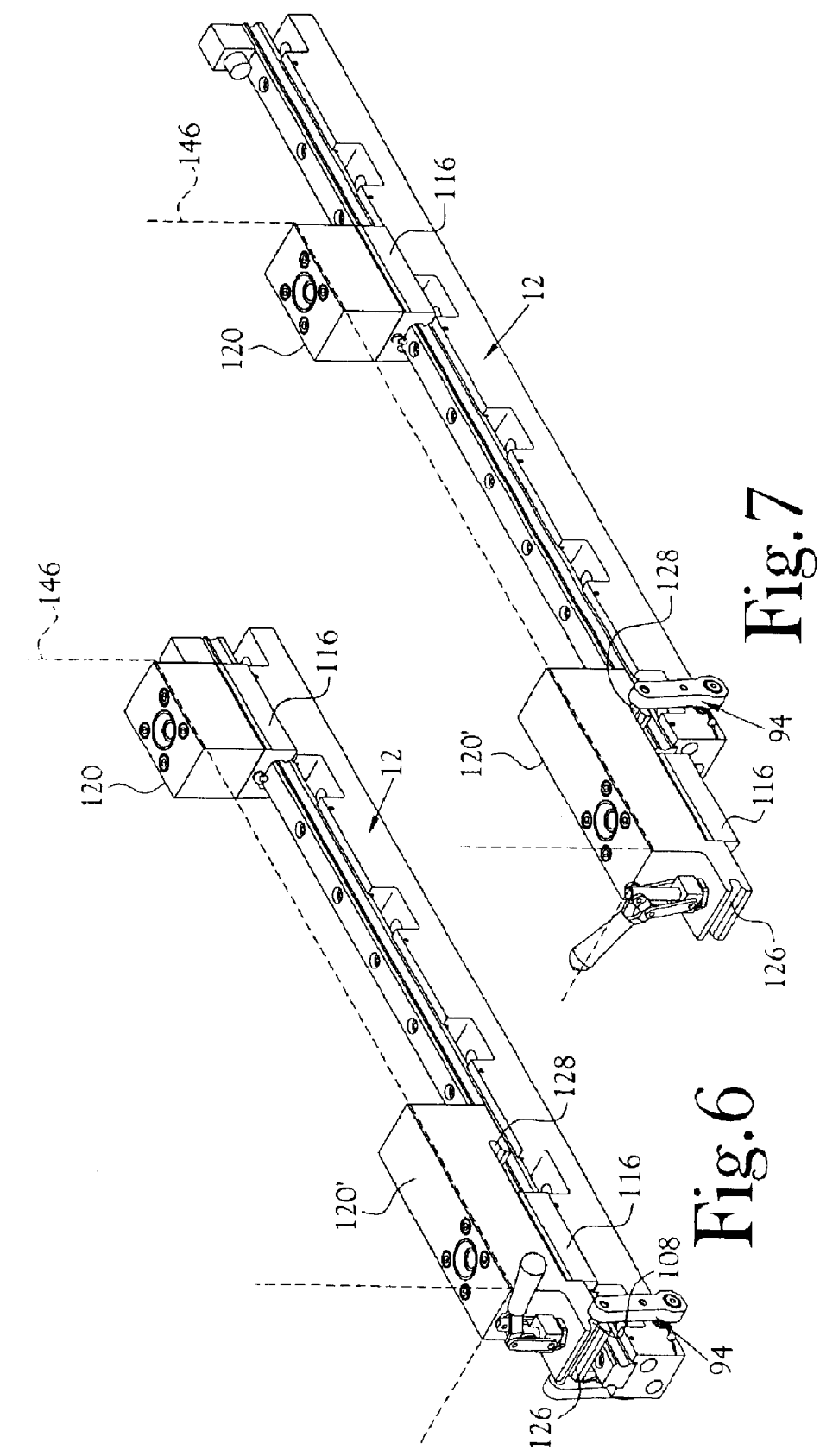

RAIL SYSTEM FOR SUPPORTING AND MOVING A PATIENT GANTRY

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

The present invention pertains to the field of medical imaging. More particularly, the present invention is a rail system for supporting and moving a patient gantry, wherein a portion of the rail system is removable to reduce a tripping hazard when not in use.

2. Description of the Related Art

In the field of medical imaging, it is becoming more common to combine the images obtained from multi-modality scans in order to accomplish a more accurate image of a patient. For example, U.S. Pat. No. 6,490,476 issued on Dec. 3, 2002, to D. W. Townsend et al., discloses a combined PET and X-ray CT tomograph and method for using same. As discussed by Townsend et al., the role of PET imaging in oncology research and patient care is growing, and the ability of PET to add unique functional information to that obtained by conventional anatomical-based modalities, such as CT and magnetic resonance (MR), is generating considerable interest. The discussion of the background art in the '476 patent is incorporated herein by reference.

In recent years, there has been considerable progress in the development of techniques to co-register and align functional and anatomical images. This has been driven primarily by the demand for accurate localization of cerebral function visualized in PET studies where the low resolution morphology is, in most cases, insufficient to identify the related cerebral structures. After two images from different modalities are aligned they can be displayed in a number of ways, such as, for example, side by side with linked cross-hair cursors, so that positional correspondence between the two image sets is easily established.

The '476 device is directed to an X-ray CT and PET tomograph having a physically known relationship one with the other. Each of the X-ray CT and PET tomograph are configured for use with a single patient bed such that a patient may be placed on the bed and moved into position for either or both of an X-ray CT scan and a PET scan. In one embodiment, X-ray CT and PET tomograph detectors are disposed in separate gantries which are fixed relative to each other, and wherein the patient bed is movable between the gantries. In another embodiment, the X-ray and PET tomograph detectors are disposed in separate gantries, either of which is movable with respect to the other.

One problem that arises with these configurations is servicing the imaging devices. With the two devices situated next to each other, the rearward device must be pulled away from the forward device in order to service the forward device. The current method used to pull the PET device from the CT device includes permanently mounting a bearing plate in the floor and using a winch to pull the PET device along the bearing plate. Thus, moving the PET device is a complicated task.

In addition to servicing the imaging devices, as disclosed by Townsend et al., moving the imaging devices is in some situations necessary for acquiring images. While the devices may be mounted on wheels, a specific path must be defined through which the imaging device travels in order to accurately position the imaging devices to acquire images that can be co-registered with minimal correction.

BRIEF SUMMARY OF THE INVENTION

The present invention is a rail system for supporting a patient gantry associated with a medical imaging device. The rail system includes primarily a fixed rail assembly and a service rail assembly. The fixed rail assembly is permanently mounted on the support surface and the service rail assembly is releasably securable to the fixed rail assembly in an end-to-end fashion. Each of the fixed rail assembly and the service rail assembly includes primarily a longitudinal bar on which is mounted a top rail.

The fixed bar defines a series of recesses and a through opening in each recess. The openings are provided for receiving a bolt used to secure the fixed bar to the support surface. A disc spring and nut are provided with each bolt. The recesses are configured to receive the disc spring and nut.

A plurality of levelers is provided for leveling the service rail, each leveler including a foot for engaging the support surface and carrying a threaded bolt. A disc spring and a nut are provided with each leveler for securing the leveler in place. Similar to the fixed bar, the service bar defines a series of recesses. A threaded opening is defined in each recess for receiving and cooperating with the leveler threaded bolt. A disc spring and nut are provided for securing each leveler in place once adjusted, the recesses being configured to receive the disc spring and nut.

A longitudinal recess is defined in the top surface of each of the fixed bar and the service bar for receiving a top rail. A series of threaded openings are defined in each of the fixed bar and the service bar to cooperate with a series of through openings defined in the top rail, each for receiving and engaging a mounting screw.

An alignment device is provided for accurately aligning the top rail of the service rail assembly with the top rail of the fixed rail assembly. The alignment device includes a plurality of bushings recessed in the distal end of the fixed bar and a plurality of pin dowels carried by the proximal end of the service bar. The pin dowels are configured to be received within the bushings. The bushings and pin dowels are disposed in selected patterns so that service rails cannot be interchanged with other fixed rails, as each service rail assembly is leveled for the specific location on the support surface on which it is engaged.

A locking mechanism is provided for positively securing the service rail assembly to the fixed rail assembly when the pin dowels are engaged within the bushings. A safety lever defines a substantially U-shaped configuration having two parallel arms pivotally mounted on either side of the distal end of the fixed bar. A cross member extends between the distal ends of the parallel arms and is received in a cross member receptor defined under the proximal end of the service bar. The safety lever is biased upwardly to accomplish a positive engagement between the cross member and the receptor.

Two bearing blocks are provided for sliding on the top rail of each of the fixed rail assembly and the service rail assembly. Each bearing block defines a channel configured to receive the top rails. Each bearing block is provided with a plurality of ball bearings to accomplish sliding movement along the top rails. A mounting block is secured to each bearing block, and is provided for mounting the patient gantry.

Several safety mechanisms are provided for preventing movement of the patient gantry with respect to the fixed rail assembly when the service rail assembly is removed. First, a toggle clamp is carried by the second mounting block and includes a pin articulately connected to a lever. The lever is pivotally connected to a frame mounted on the second mounting block. As the lever is pivoted, the pin is moved axially in a vertical direction. A locating hole is defined in the distal end of the fixed rail assembly top rail for closely receiving the pin. The locating hole is disposed at a location such that when the pin is engaged, the patient gantry is properly positioned.

The second safety mechanism is provided for the situation where the toggle clamp has been inadvertently disengaged. The distal end of the second mounting block defines a first receptor for receiving the safety lever cross member. When the service rail assembly is removed from engagement with the fixed rail assembly, the spring biases the safety lever upward so that the cross member is received within the second mounting block first receptor. For the unlikely event that the toggle clamp has not been engaged and the safety lever does not engage the second mounting block first receptor, the second mounting block defines a second receptor adapted to receive the safety lever cross member. The second receptor is defined on the bottom of the second mounting block at the proximal end thereof. As the patient gantry is moved toward the proximal end to the distal end of the fixed rail assembly, the second mounting block begins to become disengaged from the top rail. However, the spring biases the safety lever upward and the cross member eventually engages the second mounting block second receptor. While the patient gantry becomes partially derailed, further derailment is prevented and the work required to remount the patient gantry on the rail system is minimized.

In order to prevent unselected removal of the bearing blocks from either of the top rails, a bumper block is provided at each of the proximal end of the fixed rail assembly top rail and the distal end of the service rail assembly top rail. A bumper is mounted on each bumper block and is oriented toward the center of the rail system.

BRIEF DESCRIPTION OF THE SEVERAL VIEWS OF THE DRAWINGS

The above-mentioned features of the invention will become more clearly understood from the following detailed description of the invention read together with the drawings in which:

FIG. 1 is a perspective illustration of a rail system for supporting a patient gantry associated with a medical imaging device constructed in accordance with several features of the present invention;

FIGS. 5A–5C illustrate the operation of a toggle clamp incorporated in the rail system of FIG. 1;

FIG. 6 is a perspective illustration of the fixed rail assembly of FIG. 1 showing the safety lever engaged with the first receptor of the second mounting block; and FIG. 7 is a perspective illustration of the fixed rail assembly of FIG. 1 showing the safety lever engaged with the second receptor of the second mounting block.

DETAILED DESCRIPTION OF THE INVENTION

A rail system for supporting a patient gantry associated with a medical imaging device is provided. The rail system of the present invention is further provided for assisting in moving the patient gantry when required. When the patient gantry in secured in place, a service rail is removable in order to eliminate tripping hazards and minimize space requirements of the medical imaging system. When the portion of the rail system is removed, a locking mechanism prevents the patient gantry from being inadvertently derailed from a fixed rail portion.

Figure 2A:
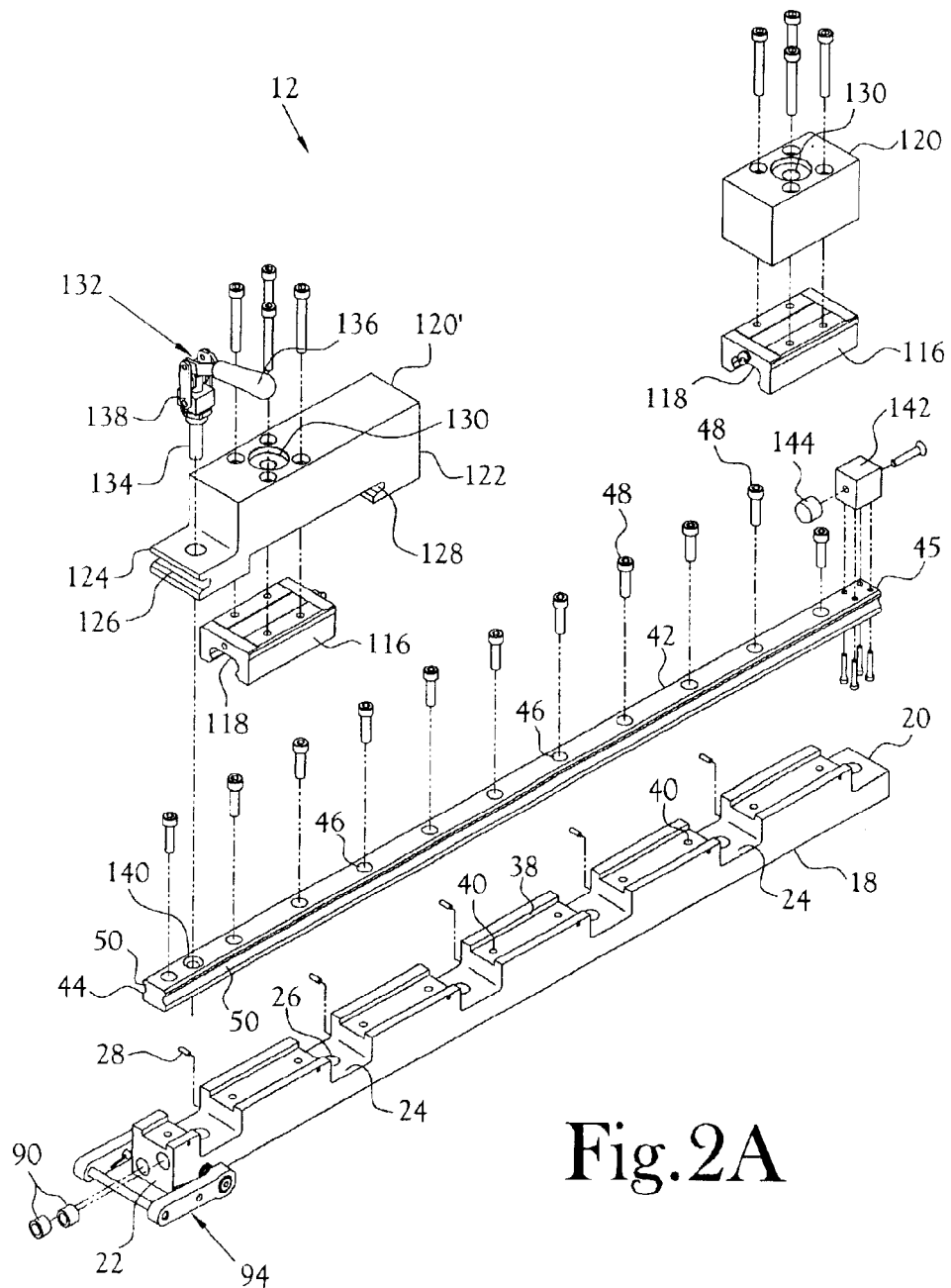
FIG. 2A is an exploded view, in perspective, of the fixed rail assembly of the rail system illustrated in FIG. 1.
Figure 2B:
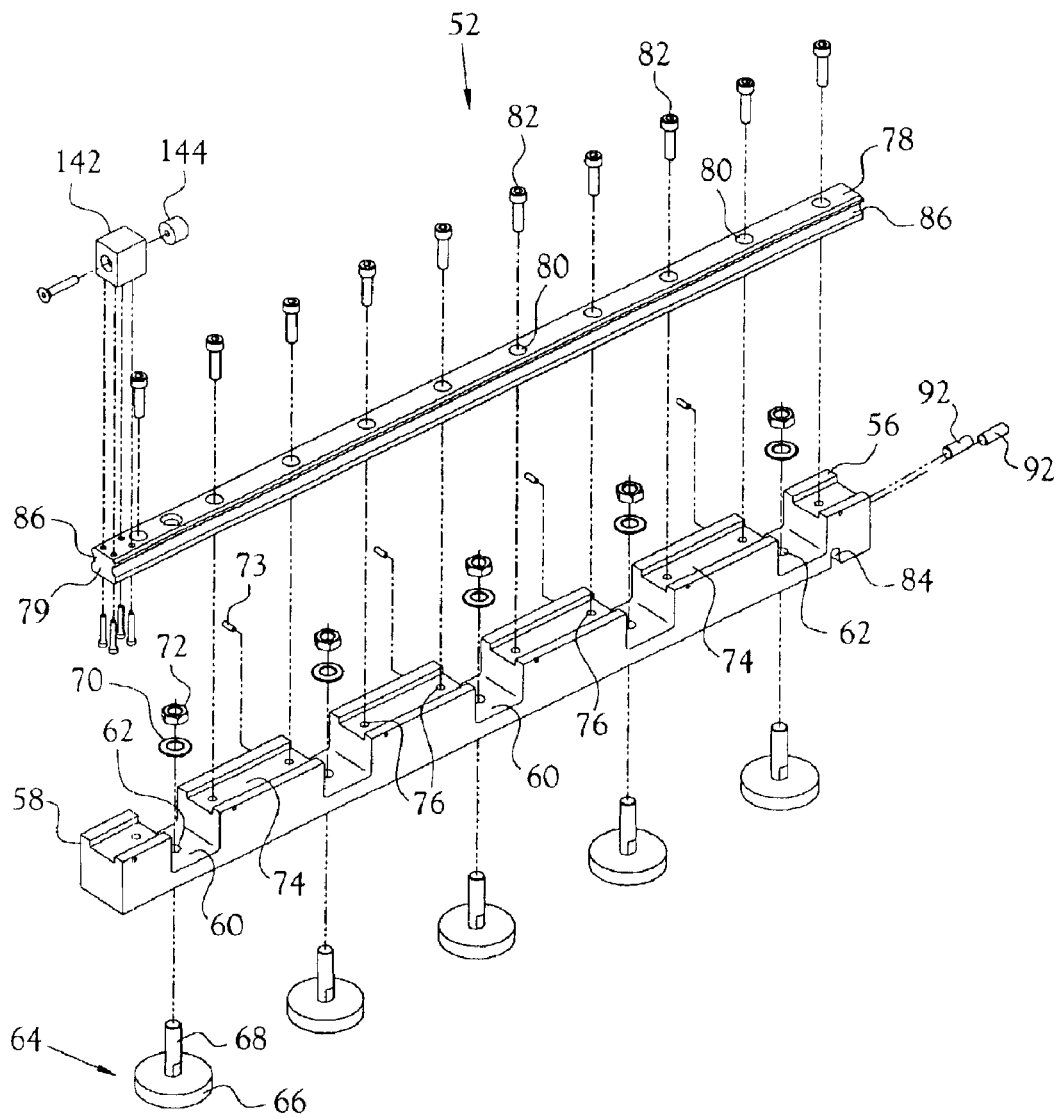
FIG. 2B is an exploded view, in perspective, of the service rail assembly of the rail system illustrated in FIG. 1.

The rail system in illustrated generally at 10 in the figures. FIG. 1 is a perspective illustration of the rail system 10. FIGS. 2A and 2B are exploded views of the rail system 10, illustrating the relationship between the various elements thereof. Referring to FIGS. 1, 2A and 2B, the rail system 10 includes primarily a fixed rail assembly 12, illustrated in greater detail in FIG. 2A, and a service rail assembly 52, illustrated in greater detail in FIG. 2B. The fixed rail assembly 12 is permanently mounted on the support surface and the service rail assembly 52 is releasably securable to the fixed rail assembly 12 in an end-to-end fashion. Each of the fixed rail assembly 12 and the service rail assembly 52 includes primarily a longitudinal bar 18,54 on which is mounted a top rail 42,78, respectively.

Referring to FIG. 2A, the fixed bar 18 defines a series of recesses 24. A through opening 26 is defined in each recess 24. The openings 26 are provided for receiving a bolt (not shown) used to secure the fixed bar 18 to the support surface. The recesses 24 are configured to receive a disc spring and nut (not shown) associated with the bolt.

A longitudinal recess 38 is defined in the top surface of the fixed bar 18. A top rail 42 is received within the longitudinal recess 38 and secured to the fixed bar 18, as more clearly illustrated in FIGS. 3A and 3B. The longitudinal recess 38 serves to align the top rail 42 with the fixed bar 18. Referring again to FIG. 2, a series of threaded openings 40 are defined in the fixed bar 18 to cooperate with a series of through openings 46 defined in the top rail 42. A mounting screw 48 is received through each top rail through opening 46 and engaged within each fixed bar threaded opening 40 to secure the top rail 42 to the fixed bar 18. At least one set screw 28 is provided for preventing an associated mounting screw 48 from disengaging.

As best illustrated in FIG. 2B, a plurality of levelers 64 is provided for leveling the service rail assembly 52. Each leveler 64 includes a foot 66 carrying a threaded bolt 68. The foot 66 is configured to engage the support surface. A disc spring 70 and a nut 72 are provided with each leveler 64 for securing the leveler 64 in place.

The service bar 54 likewise defines a series of recesses 60. A threaded opening 76 is defined in each recess 60 for receiving and cooperating with the leveler threaded bolt 68. Each leveler 64 is adjusted by rotating the threaded bolt 68 in either direction until the foot 66 is firmly engaged on the support surface and the service bar 54 is level. A disc spring 70 and nut 72 are provided for securing each leveler 64 in place once adjusted. The recesses 60 are configured to receive the disc spring 70 and nut 72.

A longitudinal recess 74 is defined in the top surface of the service bar 54 for receiving a top rail 78. A series of threaded openings 76 are defined in the service bar 54 to cooperate with a series of through openings 80 defined in the top rail 78. A mounting screw 82 is received through each top rail through opening 80 and engaged within each service bar threaded opening 76 to secure the top rail 78 to the service bar 54. At least one set screw 73 is provided for preventing an associated mounting screw 82 from disengaging.

Referring again to FIG. 2A, at least two bearing blocks 116 are provided for sliding on the top rail 42,78 of each of the fixed rail assembly 12 and the service rail assembly 52. Each bearing block 116 defines a channel 118 configured to receive the top rails 42,78. In the illustrated embodiment, the top rails 42,78 define longitudinal grooves 50,86 on either side thereof. The bearing block channel 118 is adapted to be received within each of the top rail longitudinal grooves 50,86 such that the bearing block 116 is limited to linear movement along the top rails 42,78. Each bearing block 116 is provided with a plurality of ball bearings (not illustrated) to accomplish sliding movement along the top rails 42,78. The bearing block 116 of the preferred embodiment incorporates a conventional linear ball bearing in which at least one horizontal circuit of ball bearings on either side of the bearing block channel 118.

A mounting block 120 is secured to each bearing block 116, and is provided for mounting the patient gantry 146. Illustrated is a first mounting block 120 secured to the front 148 of the patient gantry 146 and a second mounting block 120' secured to back 150 of the patient gantry 146. A leveling screw 130 is provided on each mounting block 120 to level the patient gantry 146 with respect to the rail system 10.

In order to prevent unselected removal of the bearing blocks 116 from either of the top rails 42,78, a bumper block 142 is provided at each of the proximal end 45 of the fixed rail assembly top rail 42 and the distal end 79 of the service rail assembly top rail 78. A bumper 144 is mounted on each bumper block 142 and is oriented toward the center of the rail system 10.

Figure 3:
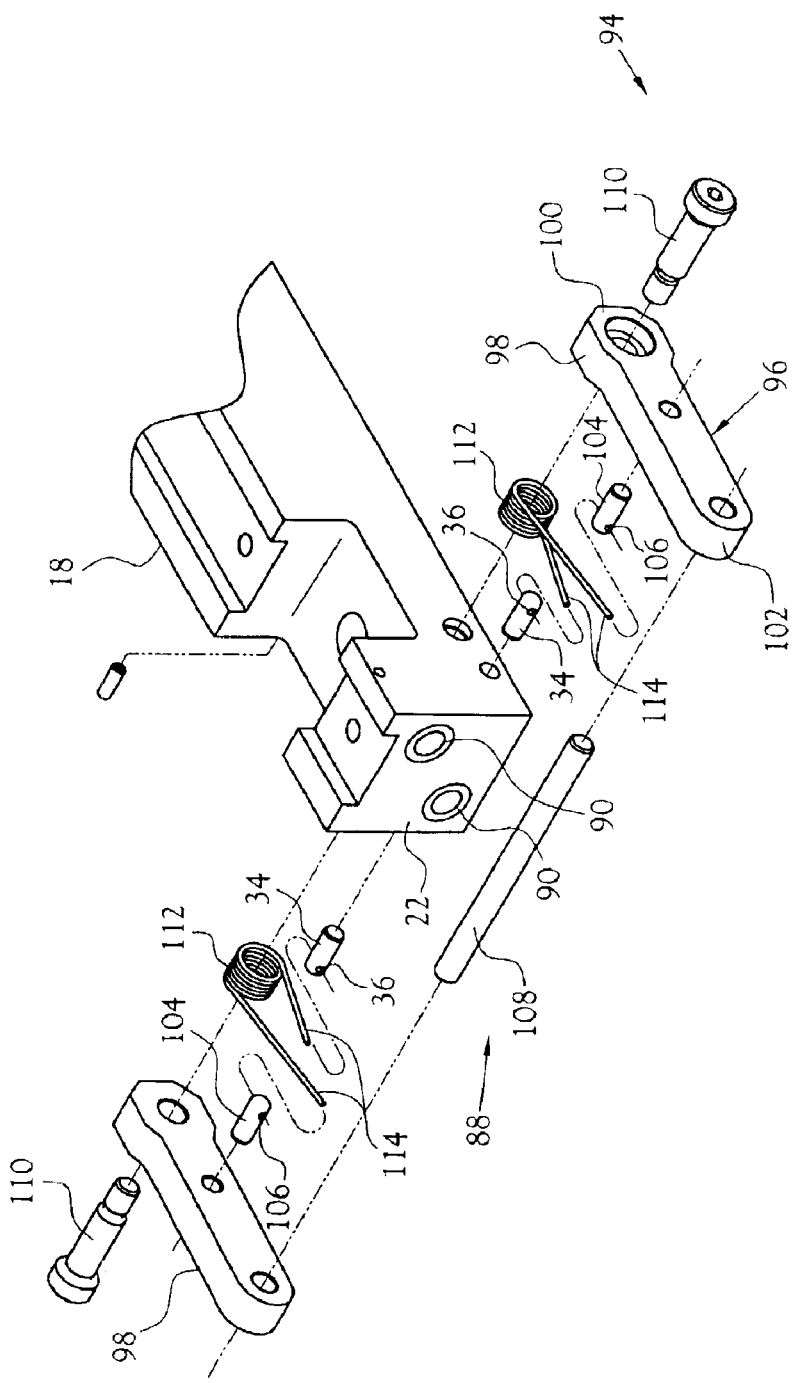
FIG. 3 is an exploded view, in perspective, of a locking mechanism configured to lock the service rail assembly of FIG. 2B to the fixed rail assembly of FIG. 2A.

Illustrated in FIG. 3 is a locking mechanism 94 provided for positively securing the service rail assembly 52 to the fixed rail assembly 12 when the pin dowels 92 are engaged within the bushings 90. A safety lever 96 defines a substantially U-shaped configuration having two parallel arms 98 disposed on either side of the distal end 22 of the fixed bar 18. A cross member 108 extends between the distal ends 102 of the parallel arms 98 and is received under the proximal end 56 of the service bar 54 when the service rail assembly 52 and fixed rail assembly 12 are engaged. A screw or pin 110 is carried by the proximal end 100 of each of the parallel arms 98 and is mounted in the fixed bar 18 to allow the safety lever 96 to pivot about the pins 110.

The safety lever 96 is biased upwardly via a spring 112. A spring pin 104 is carried by each lever arm 98, and a spring pin 34 is carried on either side of the distal end 22 of the fixed bar 18. Each of the spring pins 104,34 defines a through opening 106,36 for receiving one arm 114 of a compression spring 112 carried on the pin 110 used to mount the safety lever 96.

A safety lever receptor 84 is defined on the lower surface of the proximal end 56 of the service bar 54 for positively seating the safety lever cross-member 108. When the alignment device 88 as described is properly engaged, the safety lever cross member 108 is received within receptor 84 to lock the relative positions of the fixed rail assembly 12 and the service rail assembly 52. The service rail assembly 52 is removed from engagement with the fixed rail assembly 12 by lowering the safety lever 96 and pulling the service rail assembly 52 in an axial direction away from the fixed rail assembly 12.

Figure 4A:
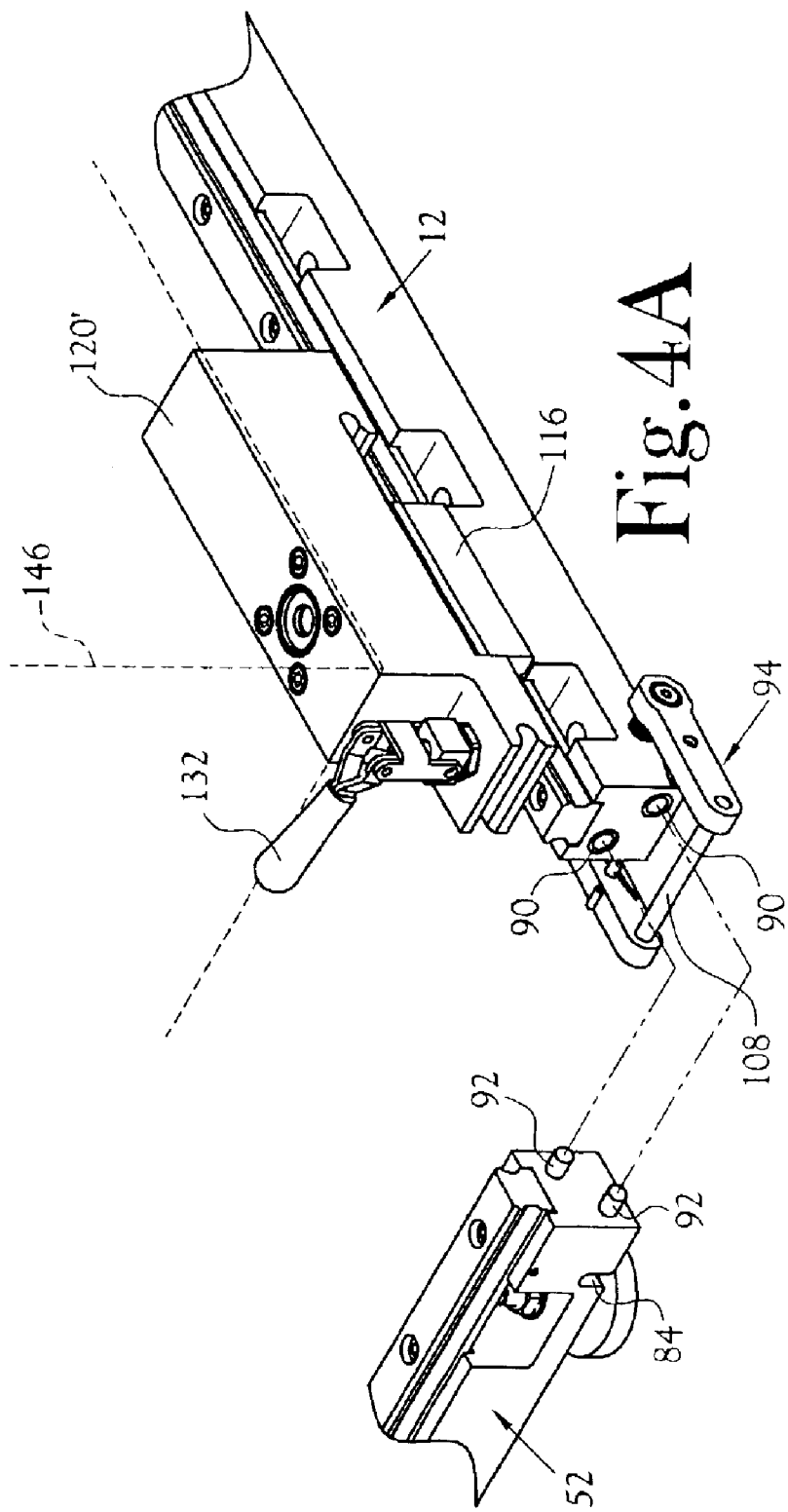
FIG. 4A is a perspective illustration of the proximal end of a service rail assembly and the distal end of a fixed rail assembly in accordance with the present invention, showing an alignment device of a first configuration.
Figure 4B:
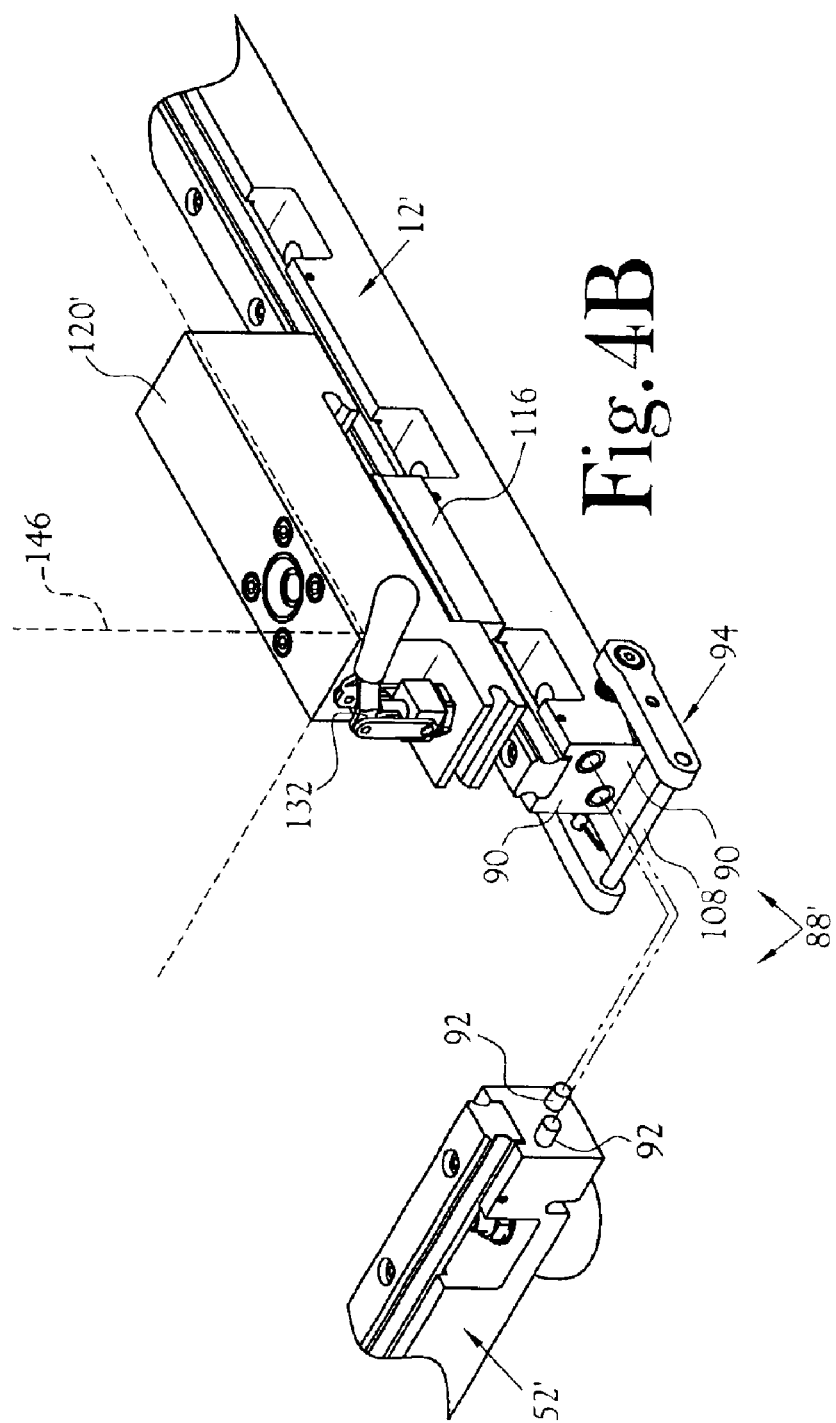
FIG. 4B is a perspective illustration of the proximal end of a service rail assembly and the distal end of a fixed rail assembly in accordance with the present invention, showing an alignment device of a second configuration so as to preclude interchanging service rail assemblies between rail systems.

As disclosed above, the service rail assembly 52 is releasably securable to the fixed rail assembly 12. As best illustrated in FIGS. 4A and 4B, an alignment device 88 is provided for accurately aligning the top rail 78 of the service rail assembly 52 with the top rail 42 of the fixed rail assembly 12. The alignment device 88 of the illustrated embodiment includes a plurality of bushings 90 recessed in the distal end 22 of the fixed bar 18 and a plurality of pin dowels 92 carried by the proximal end 56 of the service bar 54. The pin dowels 92 are configured to be received within the bushings 90 in the distal end 22 of the fixed bar 18. FIGS. 4A and 4B illustrate, in perspective, the proximal end of two service rail assemblies 52,52' and the distal end of two fixed rail assemblies 12,12' of the present invention. These figures more clearly illustrate that the bushings 90 and pin dowels 92, are disposed in selected patterns such that the service rail assembly 52 is not interchangeable with the service rail assembly 52', as each service rail assembly 52,52' is leveled for the specific location on the support surface on which it is engaged. In the illustrated embodiment, a mirror-imaged asymmetric pattern is used. However, it will be understood that other patterns accomplish the same result.

Several safety mechanisms are provided for preventing movement of the patient gantry 146 with respect to the fixed rail assembly 12 when the service rail assembly 152 is removed. First, a toggle clamp 132 is carried by the second mounting block 120'. FIGS. 5A–5C illustrate the operation of the toggle clamp 132. The toggle clamp 132 includes a pin 134 articulately connected to a lever 136. The lever 136 is pivotally connected to a frame 138 mounted on the second mounting block 120'. As the lever 136 is pivoted, the pin 134 is moved axially in a vertical direction. A locating hole 140 is defined in the distal end 44 of the fixed rail assembly top rail 42 for closely receiving the pin 134. The locating hole 140 is disposed at a location such that when the pin 134 is engaged, the patient gantry 146 is properly positioned. FIG. 5A illustrates the lever 136 in an engaged orientation and the pin 134 received within the locating hole 140. FIG. 5B illustrates an intermediate orientation of the lever 136. Finally, FIG. 5C illustrates the lever 136 in an unengaged orientation and the pin 134 retracted from the locating hole 140, thereby allowing lineal movement of the patient gantry 146. In the preferred embodiment, the orientation of the toggle clamp 132 is mirrored between left- and right-hand rail systems 10.

The second safety mechanism is provided for the situation where the toggle clamp 132 has been inadvertently disengaged. As illustrated in FIG. 6, the distal end 124 of the second mounting block 120' defines a first receptor 126 for receiving the safety lever cross member 108. When the service rail assembly 52 is removed from engagement with the fixed rail assembly 12, the spring 112 biases the safety lever 96 upward so that the cross member 108 is received within the second mounting block first receptor 126.

Further, for the unlikely event that the toggle clamp 132 has not been engaged and the safety lever 96 does not engage the second mounting block first receptor 126, the second mounting block 120' defines a second receptor 128 adapted to receive the safety lever cross member 108, as best illustrated in FIG. 7. The second receptor 128 is defined on the bottom of the second mounting block 120' at the proximal end 122 thereof. As the patient gantry 146 is moved toward the proximal end 14 to the distal end 16 of the fixed rail assembly 12, the second mounting block 120' begins to become disengaged from the top rail 42. However, the spring 112 biases the safety lever 96 upward and the cross member 108 eventually engages the second mounting block second receptor 128. While the patient gantry 146 becomes partially derailed, further derailment is prevented and the work required to remount the patient gantry 146 on the rail system 10 is minimized.

At least two rail systems 10 are utilized in cooperation with each other to support a patient gantry 146 associated with a medical imaging device. In the preferred embodiment, two rail systems 10 are used, with one being disposed at either end of the patient gantry 146. As described, the alignment device 88 for each rail system 10 defines a unique configuration so that the service rail assemblies 52 cannot be interchanged between rail systems 10. Further, the toggle clamps 132 for the rail systems 10 are oriented in opposite directions such that one can visually detect whether the toggle clamps 132 are properly engaged. Although not illustrated, a cover panel adapted to cover the distal ends 16 of the fixed rail assemblies 12 and extend between the bottom of the patient gantry 146 and the support surface is configured to be mounted on the patient gantry 146 only if both of the toggle clamps 132 are properly engaged.

While the rail system 10 of the present invention has been described and illustrated as providing straight rail assemblies 10, it will be understood that curved rail systems may be provided as well. Further, while a single service rail assembly 52 is disclosed with each fixed rail assembly 12, it will be understood that more than one service rail assembly 52 may be secured in an end-to-end fashion to accomplish a rail system 10 of any desired length. Each connection between pairs of rail assemblies is accomplished by an alignment device 88 having a unique dowel pin 92 and bushing 90 pattern compared to each other alignment device 88.

To install the rail system 10 of the present invention, both the fixed rail assembly 12 and the service rail assembly 52 must be leveled with respect to each other. The patient gantry 146 must also be leveled. In order to reduce installation time in the field, the patient gantry 146 is leveled with respect to the fixed rail assembly 12 during manufacture. The fixed bar 18 is then leveled in the field using conventional methods, such as with lasers, and is then secured to the support surface. The service bar 54 is then leveled by manipulating the levelers 64.

After each of the fixed bar 18 and service bar 54 has been leveled, the top rails 42,78 are mounted. The bearing blocks 116 and mounting blocks 120 are then installed, and the patient gantry 146 is mounted. The patient gantry 146 is positioned on the fixed rail assembly 12 and the toggle clamp 132 is manipulated to insert the toggle pin 134 in the locating hole 140.

The safety lever 96 is then rotated downward and the service rail assembly 52 pulled away from the fixed rail assembly 12. The service rail assembly 52 is them pulled away from the fixed rail assembly 12 and the safety lever 96 is released. The safety lever 96 then engages the second mounting block first receptor 126 which, along with the toggle clamp 132, prevents movement of the patient gantry 146.

To reinstall the service rail assembly 52, the safety lever 96 is rotated downward to be received under the proximal end 56 of the service bar 54. The dowel pins 92 are then inserted into the bushings 90 and the service rail assembly 52 is pushed into engagement with the fixed rail assembly 12. The safety lever 96 is then released. The toggle clamp 132 is then actuated to remove the pin 134 from within the location hole 140 and the patient gantry 146 is released to axial movement.

From the foregoing description, it will be recognized by those skilled in the art that a rail system for supporting and moving a patient gantry having advantages over the prior art has been disclosed. The rail system of the present invention is provided for assisting in moving the patient gantry when required. The rail system is configured to be separable such that when the patient gantry in secured in place, a service rail is removable in order to eliminate tripping hazards and minimize space requirements of the medical imaging system. Several safety features are incorporated to prevent unselected movement of the patient gantry and derailment thereof from the rail system.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A rail system for supporting a patient gantly associated with a medical imaging device, said rail system comprising:
    a fixed rail assembly mounted on a support surface, said fixed rail assembly including a fixed bar and a top rail mounted on said fixed bar;
    a service rail assembly releasably securable to said fixed rail assembly in an end-to-end fashion, said service rail assembly including a service bar and a top rail mounted on said service bar;
    a plurality of levelers for leveling said service rail assembly on the support surface, each of said plurality of levelers including a foot configured to engage the support surface, a threaded bolt carried by said foot, a disc spring and a nut, said service bar defining a plurality of recesses, a threaded opening being defined in each of said plurality of recesses for receiving and engaging said leveler threaded bolt to adjust a level of said foot, each of said plurality of recesses being configured to receive said disc spring and said nut; and
    an alignment device for aligning said service rail assembly top rail with said fixed rail assembly top rail.

2. The rail system of claim 1 wherein said fixed bar defines a plurality of recesses, a through opening being defined in each of said plurality of recesses for receiving a conventional fastener for securing said fixed bar to the support surface, each of said plurality of recesses being configured to receive a portion of said conventional fastener.

3. The rail system of claim 1 further comprising a locking mechanism for positively securing said service rail assembly to said fixed rail assembly when said alignment device is engaged.

4. A rail system for supporting a patient gantry associated with a medical imaging device, said rail system comprising:
   a fixed rail assembly mounted on a support surface, said fixed rail assembly including a fixed bar and a top rail mounted on said fixed bar;
   a service rail assembly releasably securable to said fixed rail assembly in an end-to-end fashion, said service rail assembly including a service bar and a top rail mounted on said service bar;
   an alignment device for aligning said service rail assembly top rail with said fixed rail assembly top rail; and
   a locking mechanism for positively securing said service rail assembly to said fixed rail assembly when said alignment device is engaged, said locking mechanism including:
      a lever defining a substantially U-shaped configuration having two parallel arms pivotally mounted on either side of a distal end of said fixed bar, said lever further including a cross member extending between a distal end of each of said two parallel arms and configured to be received under a proximal end of said service bar when said service rail assembly and said fixed rail assembly are engaged, a mounting device being carried by a proximal end of each of said two parallel arms and being mounted in said fixed bar to allow said lever to pivot about said mounting device;
      a compression spring disposed on each side of said fixed rail, said compression spring defining a coiled portion and two extending arms, said coiled portion being received on said mounting device;
      a spring pin carried by each of said two parallel arms and on either side of said fixed rail, each said spring pin defining a through opening for receiving one of said compression spring two extending arms, said spring being provided for biasing said lever upward relative to the support surface; and
      a receptor defined on a lower surface of said proximal end of said service bar and configured for positively seating said lever cross member.

5. The rail system of claim 4 further comprising at least one bearing block adapted to be received on each of said fixed rail assembly top rail and said service rail assembly top rail, said at least one bearing block being configured to be limited to axial movement along each of said fixed rail assembly top rail and said service rail assembly top rail.

6. The rail system of claim 5 further comprising at least one mounting block secured to each said at least one bearing block, said at least one mounting block being provided for mounting the patient gantry on said rail system.

7. The rail system of claim 6 wherein a first said bearing block is disposed proximate a front of the patient gantry and on which is mounted a first said mounting block and wherein a second said bearing block is disposed proximate a back of the patient gantry and on which is mounted a second said mounting block, said second mounting block defining a distal end which defines a first receptor configured for positively seating said lever cross member when said service rail assembly is disengaged from said fixed rail assembly.

8. The rail system of claim 7 wherein said second mounting block further defines a second receptor on a bottom surface proximate a proximal end, said second receptor configured for positively seating said lever cross member when said service rail assembly is disengaged from said fixed rail assembly and when said lever cross member is inadvertently disengaged from said first receptor and the patient gantry is moved toward said fixed rail assembly distal end.

9. The rail system of claim 7 further comprising a toggle clamp carried by said second mounting block, said toggle clamp including a pin articulately connected to a second lever such that when said second lever is pivoted, said pin is moved vertically, said distal end of said fixed rail assembly top rail defining a locating hole for selectively receiving said pin to prevent movement of said second mounting block with respect to said fixed rail assembly.

10. The rail system of claim 5 further comprising a first bumper disposed at said fixed rail assembly proximate end and a second bumper disposed at said service rail assembly distal end, said first and second bumpers being provided for preventing derailment of the patient gantry from said fixed rail assembly top rail and said service rail assembly top rail.

11. The rail system of claim 1 further comprising at least one bearing block adapted to be received on each of said fixed rail assembly top rail and said service rail assembly top rail, said at least one bearing block being configured to be limited to axial movement along each of said fixed rail assembly top rail and said service rail assembly top rail.

12. The rail system of claim 11 further comprising at least one mounting block secured to each said at least one bearing block, said at least one mounting block being provided for mounting the patient gantry on said rail system.

13. The rail system of claim 1 wherein said fixed bar defines a longitudinal recess on a top surface thereof, said longitudinal recess being configured to receive and align said fixed rail assembly top rail, and wherein said service bar defines a longitudinal recess on a top surface thereof, said longitudinal recess being configured to receive and align said service rail assembly top rail.

14. The rail system of claim 1 wherein said alignment device includes a plurality of bushings recessed in a distal end of said fixed bar and a cooperating plurality of pin dowels carried by a proximal end of said service bar, said plurality of pin dowels being configured to be received within said plurality of bushings, whereby said service rail system top rail is aligned with said fixed rail system top rail.

15. The rail system of claim 14 wherein said plurality of bushings and said plurality of pin dowels are oriented in a unique pattern such that said service rail assembly is releasably securable only to said fixed rail assembly.

16. A rail system for supporting a patient gantry associated with a medical imaging device, said rail system comprising:
   a fixed rail assembly mounted on a support surface, said fixed rail assembly including a fixed bar and a top rail mounted on said fixed bar and defining a proximal end and a distal end;
   a service rail assembly releasably securable to said fixed rail assembly in an end-to-end fashion, said service rail assembly including a service bar and a top rail mounted on said service bar and defining a proximal end and a distal end, said service rail assembly proximal end being releasably securable to said fixed rail assembly distal end;
   a plurality of levelers for leveling said service rail assembly on the support surface, each of said plurality of levelers including a foot configured to engage the support surface, a threaded bolt carried by said foot, a disc spring and a nut, said service bar defining a plurality of recesses, a threaded opening being defined in each of said plurality of recesses for receiving and engaging said leveler threaded bolt to adjust a level of said foot, each of said plurality of recesses being configured to receive said disc spring and said nut;

an alignment device for aligning said service rail assembly top rail said fixed rail assembly top rail;

a locking mechanism for positively securing said service rail assembly to said fixed rail assembly when said alignment device is engaged;

at least one bearing block adapted to be received on each of said fixed rail assembly top rail and said service rail assembly top rail, said at least one bearing block being configured to be limited to axial movement along each of said fixed rail assembly top rail and said service rail assembly top rail;

at least one mounting block secured to each said at least one bearing block, said at least one mounting block being provided for mounting the patient gantry on said rail system; and a first bumper disposed at said fixed rail assembly proximate end and a second bumper disposed at said service rail assembly distal end, said first and second bumpers being provided for preventing derailment of the patient gantry from said fixed rail assembly top rail and said service rail assembly top rail.

17. The rail system of claim 16 wherein said fixed bar defines a plurality of recesses, a through opening being defined in each of said plurality of recesses for receiving a conventional fastener for securing said fixed bar to the support surface, each of said plurality of recesses being configured to receive a portion of said conventional fastener.

18. The rail system of claim 17 wherein said locking mechanism includes:

a lever defining a substantially U-shaped configuration having two parallel arms pivotally mounted on either side of a distal end of said fixed bar, said lever further including a cross member extending between a distal end of each of said two parallel arms and configured to be received under a proximal end of said service bar when said service rail assembly and said fixed rail assembly are engaged, a mounting device being carried by a proximal end of each of said two parallel arms and being mounted in said fixed bar to allow said lever to pivot about said mounting device;

a compression spring disposed on each side of said fixed rail, said compression spring defining a coiled portion and two extending arms, said coiled portion being received on said mounting device;

a spring pin carried by each of said two parallel arms and on either side of said fixed rail, each said spring pin defining a through opening for receiving one of said compression spring two extending arms, said spring being provided for biasing said lever upward relative to the support surface; and a receptor defined on a lower surface of said proximal end of said service bar and configured for positively seating said lever cross member.

19. The rail system of claim 18 wherein a first said bearing block is disposed proximate a front of the patient gantry and on which is mounted a first said mounting block and wherein a second said bearing block is disposed proximate a back of the patient gantry and on which is mounted a second said mounting block, said second mounting block defining a distal end which defines a first receptor configured for positively seating said lever cross member when said service rail assembly is disengaged from said fixed rail assembly.

20. The rail system of claim 19 wherein said second mounting block further defines a second receptor on a bottom surface proximate a proximal end, said second receptor configured for positively seating said lever cross member when said service rail assembly is disengaged from said fixed rail assembly and when said lever cross member is inadvertently disengaged from said first receptor and the patient gantry is moved toward said fixed rail assembly distal end.

21. The rail system of claim 19 further comprising a toggle clamp carried by said second mounting block, said toggle clamp including a pin articulately connected to a second lever such that when said second lever is pivoted, said pin is moved vertically, said distal end of said fixed rail assembly top rail defining a locating hole for selectively receiving said pin to prevent movement of said second mounting block with respect to said fixed rail assembly.

22. The rail system of claim 16 wherein said fixed bar defines a longitudinal recess on a top surface thereof, said longitudinal recess being configured to receive and align said fixed rail assembly top rail, and wherein said service bar defines a longitudinal recess on a top surface thereof, said longitudinal recess being configured to receive and align said service rail assembly top rail.

23. The rail system of claim 16 wherein said alignment device includes a plurality of bushings recessed in a distal end of said fixed bar and a cooperating plurality of pin dowels carried by a proximal end of said service bar, said plurality of pin dowels being configured to be received within said plurality of bushings, whereby said service rail system top rail is aligned with said fixed rail system top rail.

24. The rail system of claim 23 wherein said plurality of bushings and said plurality of pin dowels are oriented in a unique pattern such that said service rail assembly is releasably securable only to said fixed rail assembly.

* * * * *